(12) United States Patent
Joe et al.

(10) Patent No.: US 9,121,015 B2
(45) Date of Patent: Sep. 1, 2015

(54) PEPTIDE HAVING A VASCULARIZATION-SUPPRESSING ACTIVITY AND A USE THEREFOR

(75) Inventors: Young Ae Joe, Seoul (KR); Hyun Kyung Kim, Yongin (KR)

(73) Assignee: CATHOLIC UNIVERSITY INDUSTRY ACADEMIC COOPERATION FOUNDATION, Seoul (KR)

(*) Notice: Subject to any disclaimer, the term of this patent is extended or adjusted under 35 U.S.C. 154(b) by 0 days.

(21) Appl. No.: 13/824,789

(22) PCT Filed: Sep. 8, 2011

(86) PCT No.: PCT/KR2011/006651
§ 371 (c)(1),
(2), (4) Date: Mar. 18, 2013

(87) PCT Pub. No.: WO2012/036412
PCT Pub. Date: Mar. 22, 2012

(65) Prior Publication Data
US 2013/0184215 A1    Jul. 18, 2013

(30) Foreign Application Priority Data
Sep. 17, 2010 (KR) ........................ 10-2010-0091810

(51) Int. Cl.
| | |
|---|---|
| A61K 38/00 | (2006.01) |
| C07K 14/00 | (2006.01) |
| C12N 9/72 | (2006.01) |
| C07K 7/08 | (2006.01) |
| C07K 14/515 | (2006.01) |

(52) U.S. Cl.
CPC ............... *C12N 9/6459* (2013.01); *C07K 7/08* (2013.01); *C07K 14/515* (2013.01); *C12N 9/6462* (2013.01); *A61K 38/00* (2013.01)

(58) Field of Classification Search
CPC ...... A61K 38/00; C07K 14/00; C07K 14/515; C07K 7/08
USPC ......................................... 530/326; 514/13.3
See application file for complete search history.

(56) References Cited

U.S. PATENT DOCUMENTS

| | | | |
|---|---|---|---|
| 6,024,688 A | 2/2000 | Folkman et al. | |
| 6,509,445 B1 * | 1/2003 | Kobayashi et al. | 530/350 |
| 8,119,128 B2 * | 2/2012 | Abraham | 424/130.1 |
| 2003/0228298 A1 * | 12/2003 | Nesbit et al. | 424/94.1 |
| 2004/0052777 A1 * | 3/2004 | Nesbit et al. | 424/94.1 |
| 2006/0099671 A1 | 5/2006 | Soff et al. | |

FOREIGN PATENT DOCUMENTS

| | | |
|---|---|---|
| KR | 10-0274172 B1 | 12/2000 |
| KR | 2005/0097494 A | 10/2005 |

OTHER PUBLICATIONS

De Serrano VS, Castellino FJ, "Specific anionic residues of the recombinant kringle 2 domain of tissue-type plasminogen activator that are responsible for stabilization of its interaction with w-amino acid ligands," Biochemistry, 1993, 32, 3540-3548.*
Introduction to Cancer, from Merck manual, p. 1. Accessed Mar. 5, 2008.*
Clinical Aspects of Cancer, from Merck maual, pp. 1-4. Accessed Mar. 5, 2008.*
Auerbach R, Akhtar N, Lewis RL, Shinners BL, "Angiogenesis assays: Problems and pitfalls," Cancer and Metastasis Reviews, 2000, 19: 167-172.*
Jain RK, "Barriers to Drug Delivery in Solid Tumors," Scientific American, Jul. 1994, 58-65.*
Gura T, "Systems for Identifying New Drugs Are Often Faulty," Science, Nov. 7, 1997, 278: 1041-1042.*
Rehumatoid arthritis, from Merck manual, pp. 1-12. Accessed Sep. 16, 2009.*
Guo, Yongjing et al., "A peptide derived from the nonreceptor binding region of urokinase plasminogen activitor (uPA) inhibits tumor progression and angiogenesis and induces tumor cell death in vivo," Urokinase and Tumore Progression, The FASEB Journal, vol. 14, Jul. 2000 (pp. 1400-1410).
Kim, Hyun-Kyung, "DGDA, a local sequence of the kringle 2 domain, is a functional motif of the tissue-type plasminogen activitor's antiangiogenic kfringle domain," Biochemical and biophysical Research Communications 391 (2010) pp. 166-169.
Su, Li, "In vitro and in vivo antiangiogenic activity of a novel decapeptide derived from human tissue-type plasminogen activator kringle 2," Biochemical and Biophysical Research Communications 396 (2010) pp. 1012-1017.

* cited by examiner

*Primary Examiner* — Julie Ha
(74) *Attorney, Agent, or Firm* — Joseph Hyosuk Kim; JHK Law

(57) ABSTRACT

Provided are peptides having anti-angiogenic activity and a use thereof, and more particularly, to peptides for inhibiting angiogenesis, the peptides including amino acid sequence with potent anti-angiogenic activity, a composition for inhibiting angiogenesis, the composition including the peptides, a medicine for inhibiting angiogenesis, the medicine including the composition, and a method for inhibiting angiogenesis using the peptides. The peptides for inhibiting angiogenesis, the peptides including the amino acid sequence of the invention provides not only potent inhibitory activity on proliferation, migration and tube formation of vascular endothelial cells, but also potent in vivo anti-angiogenic activity and inhibitory activity on proliferation and migration of cancer cells. Therefore, the peptide for inhibiting angiogenesis can be efficaciously used as a treatment for various diseases including cancer with abnormal regulation of angiogenesis.

12 Claims, 6 Drawing Sheets

PEPTIDE HAVING A VASCULARIZATION-SUPPRESSING ACTIVITY AND A USE THEREFOR

CROSS-REFERENCE TO RELATED APPLICATIONS

The present application is a National Phase of and claims the benefit of PCT/KR2011/006651, with an international filing date of Sep. 8, 2011, which in turn claims priority to Korean Application No. 10-2010-0091810, filed Sep. 17, 2010, the entire disclosures of which are incorporated by reference herein.

TECHNICAL FIELD

The invention relates to peptides inhibiting angiogenic activity and a use thereof, and more particularly, to new peptides with superior in vivo anti-angiogenic activity, which also inhibit proliferation, migration and tube formation of vascular endothelial cells, and proliferation and migration of cancer cells, and a use thereof.

BACKGROUND ART

Angiogenesis is a process of forming new blood vessels from pre-existing ones, and plays an important role in normal body defense mechanisms, such as wound healing and inflammation, and physiological phenomenon and early-stage development. The angiogenesis occurs through a series of sequential steps including reconstructing vessels and generating new capillary vessels through decomposition of vascular basement membrane by proteolytic enzyme, proliferation and migration of the vascular endothelial cells that constitute vessel walls and tube (a blood-vessel) formation by differentiating the vascular endothelial cells.

In addition, the angiogenic process is strictly regulated by various negative and positive regulatory factors. However, if the angiogenic process is not regulated properly, it can accelerate various diseases including cancer, rheumathritis, or diabetic retinopathy. Abnormal angiogenesis is particularly known to play a critical role in tumor growth and metastasis; firstly, it supplies nutrients and oxygen needed for the growth and proliferation of tumor, and secondly, the new capillary vessels which invade into the tumor provide tumor cells a chance to spread to the blood circulation system, thereby enabling the tumor cells to spread all over the body.

Therefore, mechanistic studies of angiogenesis and its application in development of new inhibitors have gained increasing attention in the prevention and treatment of various diseases including cancer. In the recent years, the studies on angiogenesis inhibitor have been accelerated as the experimental animal tumor model studies and human clinical studies have confirmed that inhibition of tumor angiogenesis can effectively inhibit the growth and progress of tumors and thereby prolong patient's lifespans.

Moreover, such angiogenesis inhibitor is particularly considered to be promising in the anticancer therapy, because, firstly, the angiogenesis inhibitor can be used universally in all types of solid tumors, secondly, while the conventional anticancer chemo-therapy has toxicity on the bone marrow cells and stomach system cells with relatively faster cell cycle due to its principle of using fast growth of cancer cells, the angiogenesis inhibitor has relatively less side effects even for a long period of administration, thirdly, it is possible to suppress many cancer cells through inhibition of one blood vessel cell, because one vessel cell can supply nutrients and oxygen to hundreds of cancer cells, and fourthly, while anticancer agents have to move out of the vessel to affect cancer cells, the angiogenesis inhibitor directly contacts and acts on the endothelial cells without additional drug delivery.

Meanwhile, approximately 200 angiogenesis inhibitors have been developed so far, which can be mainly characterized into four mechanisms of: lowering activity of a specific vascular growth factor; suppressing growth or inducing death of vascular endothelial cells; suppressing the vascular growth factor or the action of indirect factors that regulate the endothelial cell survival factors; and increasing the activity of the angiogenesis inhibitor present in body. The angiogenesis inhibitors such as angiostatin, endostatin, PK5, and prothrombinkringle 2 are particularly widely known.

However, since most angiogenesis inhibitors developed so far are in the form of compounds or proteins, there are disadvantages in that it is difficult to maintain these inhibitors' good activity for a long period of time and mass-produce these inhibitors, and also a process of producing these inhibitors costs a lot. In addition, there are disadvantages in that pharmaceutical properties of these inhibitors are low, and these inhibitors may be easily denaturated.

Therefore, attempts have been recently made to develop an angiogenesis inhibitor in a peptide form to overcome the problems as described above, since peptides can be used as an effective angiogenesis inhibitor due to its molecular characteristics, such as longer plasma half-life, high resistance to degradation, high bioavaiability and excellent affinity in vivo. Among the related prior arts, Korean Patent Publication No. 2005-0097494 discloses peptide for inhibiting angiogenesis, cell migration, cell invasion and proliferation and a composition comprising such peptide, and Korean Patent Registration No. 0274172 discloses TIMP-2 derived synthetic peptide for inhibiting angiogenesis by inhibiting activity of type IV collagenase.

However, since the conventionally available angiogenic-inhibiting peptide needs more improvement in the anti-angiogenic activity effect, development of new peptides for potent angiogenesis inhibition is necessary.

DISCLOSURE

Technical Problem

Therefore, the present inventors studied for developing an angiogenesis inhibitor in a peptide form capable of preventing and treating various diseases caused by angiogenesis, and as a result, first found that peptides including amino acid sequences according to the present invention have excellent effect on suppressing angiogenesis.

Therefore, an object of the present invention is to provide peptides for inhibiting angiogenic activity, in which the peptides include a specific amino acid sequence and have excellent activity for inhibiting angiogenic activity. In addition, another abject of the present invention is to provide a composition for inhibiting angiogenic activity, the composition including such peptides as an effective component. Still another object of the present invention is to provide a method for inhibiting angiogenesis, the method comprising administrating peptides including a specific amino acid sequence according to the present invention to a mammalian animal with abnormally-continuing angiogenesis except human.

Technical Solution

In order to achieve the above-mentioned objects, the present invention provides peptides for inhibiting angiogenesis, the peptides include at least one amino acid sequence selected from the amino acid sequences represented by SEQ. ID. NO: 1 to SEQ. ID. NO: 4.

According to an embodiment of the present invention, the peptides containing the amino acid sequences represented by SEQ. ID. NO: 1 and SEQ. ID. NO: 2 may be originated from kringle domain of a tissue-type plasminogen activator, and the peptides containing the amino acid sequences represented by SEQ. ID. NO: 3 and SEQ. ID. NO: 4 may be originated from kringle domain of urokinase.

According to an embodiment of the present invention, the peptides containing the amino acid sequences represented by SEQ. ID. NO: 1 and SEQ. ID. NO: 2 may be originated from loop and beta-sheet portion of the kringle domain of the tissue-type plasminogen activator, and the peptides containing the amino acid sequences represented by SEQ. ID. NO: 3 and SEQ. ID. NO: 4 may be originated from alpha-helix and beta-sheet portion of the kringle domain of urokinase.

According to an embodiment of the present invention, the peptides may inhibit angiogenesis in vivo by inhibiting proliferation, migration and tube formation of vascular endothelial cells, and also by inhibiting proliferation and migration of cancer cells.

According to an embodiment of the present invention, the peptides may be included in a composition at concentration of 1~500 uM with respect to the total volume of the composition.

According to an embodiment of the present invention, the composition may prevent or treat a disease selected from the group consisting of: blood vessel formation-dependent cancers, benign tumors, rheumatoid arthritis, diabetic retinopathy, psoriasis, ocular angiogenesis disease, Osler-Webber Syndrome, myocardial angiogenesis, plaque neovascularization, telangiectasia, hemophilia arrthropathy, angiofibroma, trauma granulation, intestinal adhesion, atherosclerosis, scleroderma, hypertrophic scar, cat scratch disease, *Helicobacter pylori* ulcers, dialysis transplantation vascular access stenosis and obesity.

Furthermore, the present invention provides a method for inhibiting angiogenesis, the method comprising administering the peptide for inhibiting angiogenesis into a mammalian animal with abnormally-continuing angiogenesis except human.

Advantageous Effects

Since the anti-angiogenic peptides containing the amino acid sequence of the present invention can effectively inhibit migration, proliferation and tube formation of the vascular endothelial cells, and have superior activity on inhibiting proliferation and migration of cancer cells, the peptides can be efficiently used as a treatment for various diseases including cancer which has abnormally-regulated angiogenesis. Particularly, since the anti-angiogenic peptides of the present invention are provided in peptide form, rather than protein or compound forms, the peptides are easy to manufacture and mass-produce, highly resistant to degradation, and has good bioavailability and high affinity in vivo. Accordingly, the anti-angiogenic peptides of the present invention can be used as a convenient and effective angiogenesis inhibitor.

BEST MODE

Figure 1:
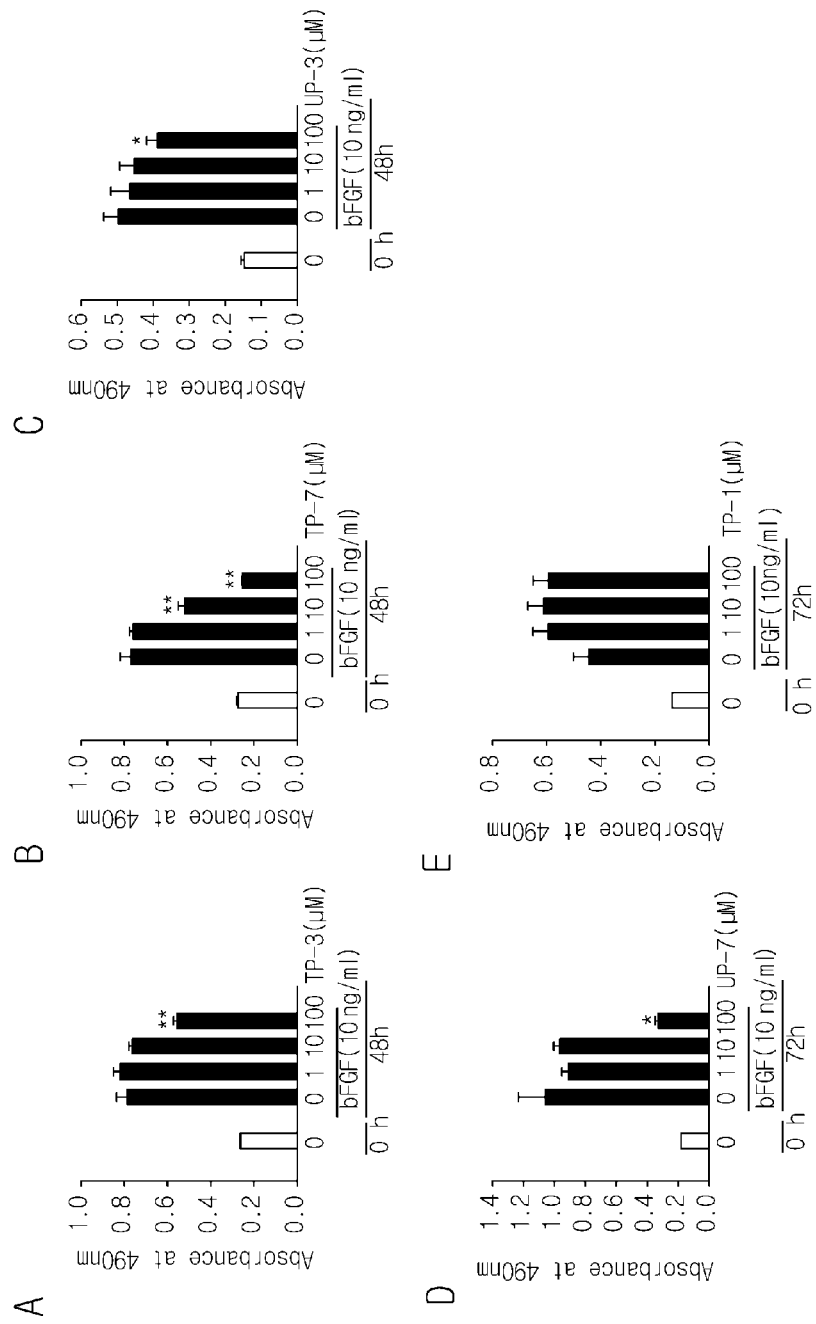
FIG. 1 is graphs illustrating measurements of cell viability by MTS assay, after plating HUVECs on a 96-well plate, treating the cells with respective peptides inn a serum-free medium for 30 min, adding bFGF and 5% FBS to the medium and incubating the cells for 48 hr (A; TP3, B; TP7, C; UP3, D; UP7, E; TP1)

The present invention provides new peptides with superior anti-angiogenic activity, and more particularly, the invention provides peptides containing amino acid sequence of PWNSMILIGKVYTAQ (SEQ ID NO: 1) or PWCHVLKNRRLTWEY (SEQ ID NO: 2) or PWNSATVLQQTYHAH (SEQ ID NO: 3) or PWCYVQVGLKPLVQE (SEQ ID NO: 4), in which the peptides have anti-angiogenic activity.

It has been demonstrated that a recombinant protein TK1-2 containing kringle of tissue type plasminogen activator (tPA) which is one of proteins related with blood clotting system, inhibits proliferation, migration tube formation of vascular endothelial cells exhibits anti-tumor effect in a xenograft animal model.

It has also been confirmed that the recombinant protein of kringle domain of urokinase which is another plasminogen activator, inhibits growth and migration of endothelial cells and also exhibits anti-tumor effect in brain tumor model. However, the above-mentioned proteins should be prepared by undergoing refolding process in vitro in order to be endowed with activity, after they are expressed in *Escherichia coli*. In addition, there is a problem in that, since the recombinant protein, TK1-2, expressed from *Pichia* is glycosylated, it could elicit antigenicity in a body and thus induces immune reaction. Therefore, the recombinant protein has disadvantages due to large molecular weight, such as metabolic instability, immune rejection response, or high manufacture cost.

Therefore, compared to the recombinant protein treatment with large molecular weights, the peptide drugs having 50 or less amino acid residues, that is, low molecular weight, has advantages in that therapeutic dose may be reduced, it may be manufactured by synthesis rather than a recombinant technique, or it may contribute to develop orally-administrable drug.

Accordingly, the present inventors identified 4 active peptides derived from TK12 kringle domain and urokinase kringle domain from the search of new peptides with superior anti-angiogenic activity.

First, the PWNSMILIGKVYTAQ peptide (SEQ. ID. NO: 1), which is one of the anti-angiogenic peptides of the present invention, exists on a site within the second kringle of TK12 that forms loop structure (Pro24~Gln36) with hydrophobicity. Another peptide, i.e., PWCHVLKNRRLTWEY (SEQ. ID. NO: 2) peptide has a structure of forming anti-parallel beta sheet (Pro61~Tyr74) and has a sequence consisting of hydrophobic amino acids. Further, the other two peptides are located in the urokinase kringle domain, contain PWNSATVLQQTYHAH (SEQ. ID. NO:3) and PWCYVQVGLKPLVQE (SEQ. ID. NO: 4), respectively, and have alpha-helix (pro24~His36) and anti-parallel beta-sheet (Pro61~Glu74) structures, respectively.

Accordingly, the invention provides anti-angiogenic peptide containing one amino acid sequence selected from the amino acid sequences represented by SEQ. ID. NO: 1 to SEQ. ID. NO: 4 and the peptide containing the amino acid sequence of the present invention may be originated from amino acid sequence coded by the genome of the entire living bodies, or synthesized by chemical methods well known in the art. Preferably, the peptides containing the amino acid sequences may be originated from the kringle domain of tissue type plasminogen activator (tPA) or from urokinase kringle domain.

Further, according to the present invention, the PWNSMILIGKVYTAQ (SEQ. ID. NO: 1) peptide is named "TP-3", the PWCHVLKNRRLTWEY (SEQ. ID. NO: 2) peptide, "TP-7", the PWNSATVLQQTYHAH (SEQ. ID. NO: 3) peptide, "UP-3", and the PWCYVQVGLKPLVQE (SEQ. ID. NO: 4) peptide, "UP-7", respectively.

The tissue type plasminogen activator (tPA) is multi-domain serine protease, and is known to be involved in the fibrinolysis and tumor cell migration. The tPA mainly includes five domains which are, from N-terminus: finger domain (F); epithelial cell proliferation factor domain (G); two kringle domains (i.e., kringle|domain, kringle||domain); and serine protease (P), in which the kringle domains consist of 70 to 80 amino acids and have unique triple-loop structure linked by disulfide bond.

Further, the kringle domain is a protein structure domain consisting of approximately 80 amino acids and 3 intramolecular disulfide bonds, and has been found in a plurality of proteins including prothrombin, plasminogen, urokinase, hepatocyte growth factor and apolipoprotein, etc. The kringle domain is known to be an independent folding unit, but none has been clarified yet about exact function thereof, except that there was a report on the use of the kringle structure as an inhibitor against migration and differentiation of the endothelial cells in the progress of angiogenesis, and particularly, on the involvement of kringle 2 of prothrombin and kringles 1 to 4 and 5 of plasminogen in anti-angiogenesis.

Urokinase functions to initiate protein degradation such as extracellular tumor matrix degradation, and thus is known to be involved in the proliferation, invasion, and migration of cells. Further, due to non-specific systemic plasminogen activation and fibrinolytic activity, urokinase has long been used as physiological thrombolytic agent and also used for deep-vein thrombosis, coronary obstructions, etc.

Meanwhile, angiogenesis is the highly-regulated process which occurs in response to not only physiological molecule such as growth factor, cytokine, but also various angiogenesis inducing factors such as hypoxia, low pH, etc. The angiogenic mechanism requires cooperation of a variety of molecules to regulate breakdown and reconstruction of ECM, migration, proliferation, differentiation and tube formation of endothelial cells to develop new vessels. After initiation of angiogenesis, the angiogenesis promoting factors such as VEGF, bFGF, IL-8 etc. activate endothelial cells by stimulating on the cell surface receptors so that the activated cells undergo cell proliferation, increased expression of cell adhesion molecules, increase secretion of protease, and increased cell migration and invasion.

Further, new blood vessels are formed as, not only the components of integrin, selectin and immunoglobulin gene super family for cell adhesion, but also a plurality of molecules including proteolytic enzyme such as matrix metaloprotease and serine protease to break down ECM promote proliferation and invasion, and as the lumen formation and differentiation into mature blood vessels are induced by a signal transmission mechanism originated from the receptors on the cell surfaces interacting with the ECM component and soluble factor.

Meanwhile, the present inventors characterized the peptides containing hydrophobic amino acids corresponding to the loop and beta-sheet structure portion from folded domains in the second kringle of TK1-2, and also characterized the peptides containing amino acids corresponding to the alpha-helix and beta-sheet structure portions in the urokinase (UK) kringle domain, to thereby analyze the remarkable anti-angiogenic activity and confirmed that the beta-sheet structure peptides consisting of hydrophobic amino acids particularly play the vital role in anti-angiogenic activity.

Generally, in terms of angiogenesis, among all the cells, the vascular endothelial cell constructing the inner layer of the vessel and directly contacting the blood plays the central role as it regulates blood vessel dilation, thrombus inhibition, and transmission and migration of selective metabolites through the vessel wall by secreting various bioactive substances, and also regulates blood flow and attachment of leukocytes and thrombocytes by expressing various membrane proteins on the surface of the cell.

Therefore the present inventors investigated whether the peptides of the present invention inhibit proliferation and migration of the vascular endothelial cells. According to an embodiment of the invention, as a result of investigating the effect of the four peptides originated from TK12 and UK1 according to the present invention and a control group which is hydrophobic TP-1 peptides exhibiting loop structure on the proliferation of the endothelial cells through MTS assay, in one embodiment, the inventors observed all the peptides of the present invention, but not the control (TP-1), exhibited inhibitory effect on the endothelial cell growth (see FIG. 1). Further, as a result of investigating the effect on the migration of the endothelial cells through modified Boyden chamber assay, the inventors could confirm that all the peptides of the present invention, but not the control (TP-1) peptides exhibited inhibitory effect on the VEGF-induced endothelial cell migration (see FIG. 2).

Figure 3:
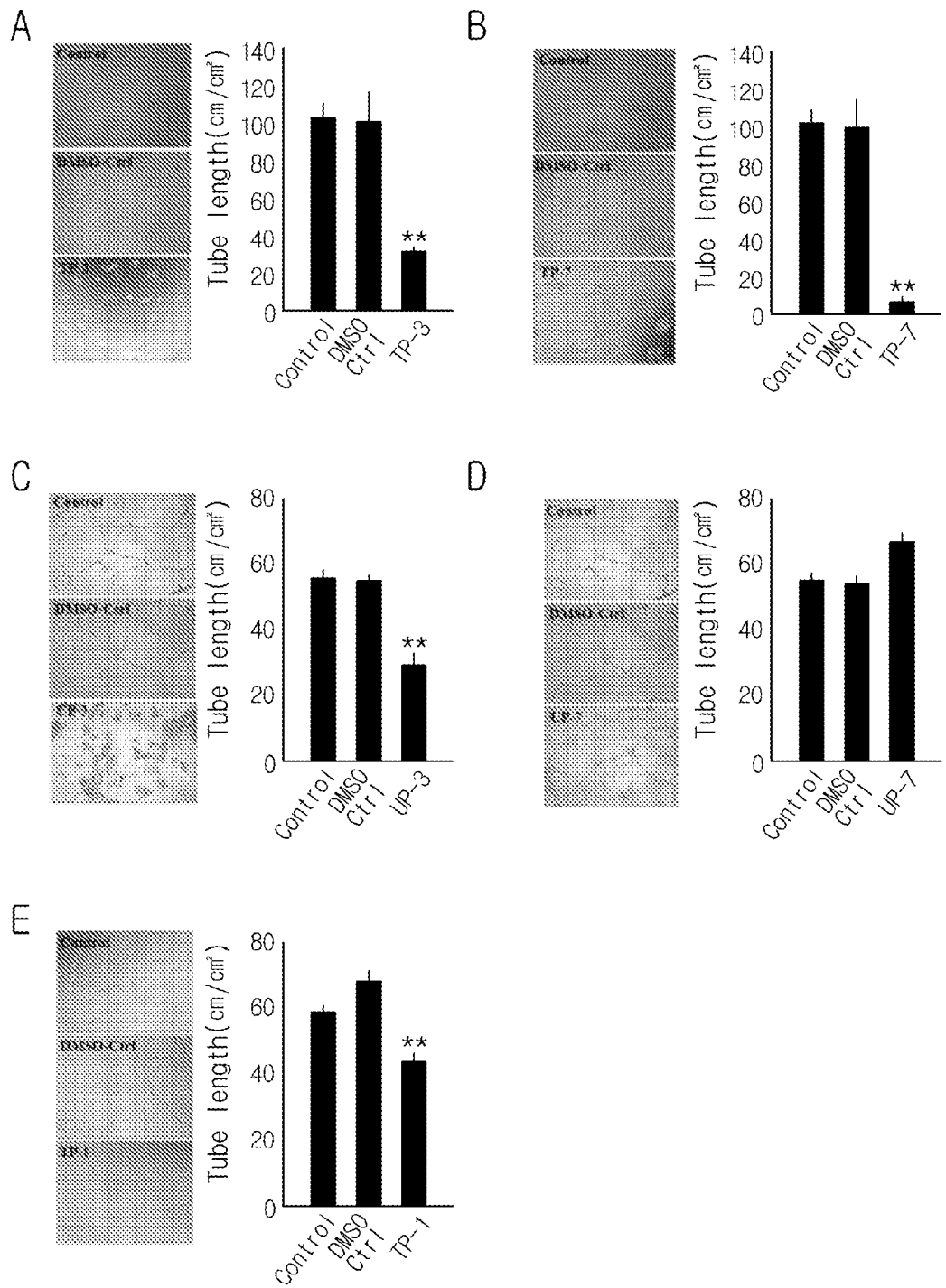
FIG. 3 is photographs illustrating tubes formed after treating HUVEC with 100 μM of respective peptides for 30 min, applying over solidified Matrigel™ and incubating for about 19 hr, along with graphs illustrating the lengths of the tubes measured using imageJ program based on the photographs (A; TP3, B; TP7, C; UP3, D; UP7, E; TP1)

Further, according to one embodiment, as a result of investigating whether the peptides of the present invention have inhibitory activity against tube formation in the angiogenesis, the inventors could confirm that, although the level of inhibition varies, all the tested peptides except UP-7 exhibited meaningful inhibitory effect against tube formation (see FIG. 3).

Figure 4:
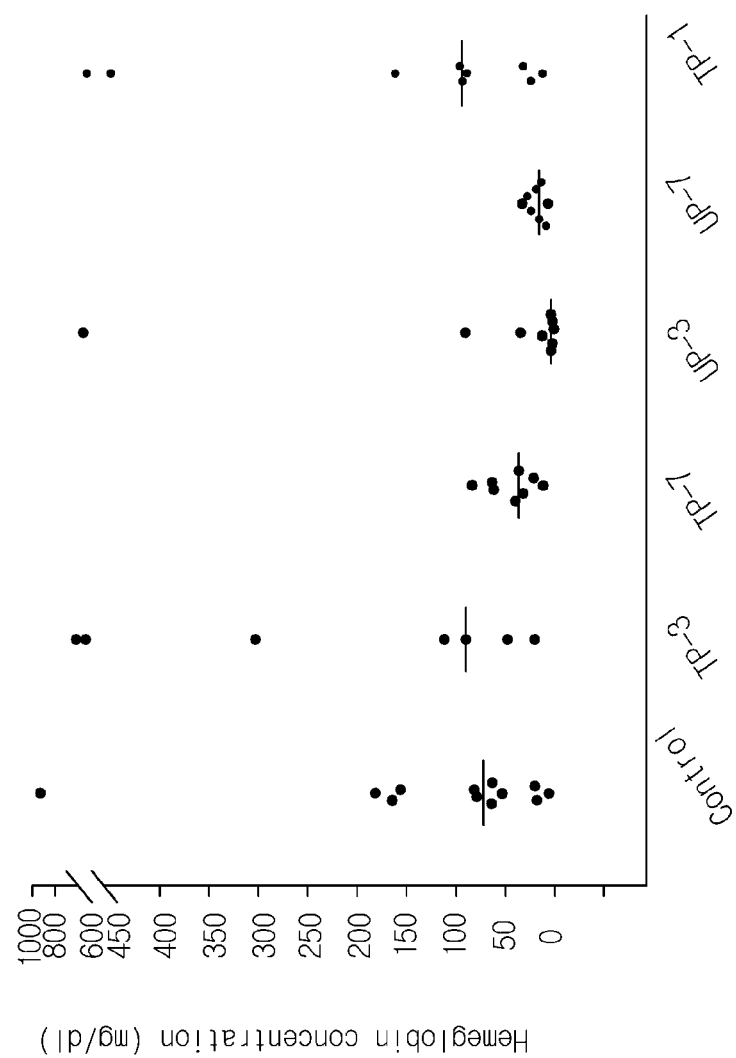
FIG. 4 is graphs illustrating quantified amount of hemoglobin of Matrigel plug, which was obtained after injecting Matrigel™ added with bFGF (100 ng/ml), VEGF (100 ng/ml) and peptides subcutaneously into mice and removing after 7 days.

Meanwhile, the present inventors investigated the effect of the peptides of the present invention on in vivo angiogenesis, and as a result of measuring the amount of hemoglobin using Matrigel plug assay, could confirm that, in one embodiment, treatment with TP-7, UP-3 and UP-7 of the peptides of the present invention exhibited decreased amount of hemoglobin and thus resulted in inhibition of angiogenesis (see FIG. 4).

Further, the present inventors investigated the effect of the peptides of the present invention on the growth of the cancer cells induced by 5% FBS, using A595 lung cancer cell lines to thus investigate whether the anti-angiogenic peptides of the present invention have the proliferation inhibition effect on not only the endothelial cells, but also the cancer cells. In one embodiment, as a result, all the TP-3, TP-7, UP-3, UP-7 peptides inhibited proliferation of cancer cells concentration-dependently (see FIG. 5). Furthermore, as a result of investigating the effect of the peptides of the present invention on the migration of cancer cell through the modified Boyden chamber assay, it was confirmed based on the cell migration test with the EGF-induced MDA-MB231 breast cells that all the peptides of the present invention inhibit cancer cell migration concentration-dependently (see FIG. 6).

Accordingly, based on the results of the above-discussed experiments, the present inventors could confirm that the peptides of the present invention provide superior inhibitory activity against proliferation, migration, and tube formation of endothelial cells, in vivo angiogenesis, and proliferation and migration of cancer cells.

Therefore, the anti-angiogenic peptides containing one amino acid sequence selected from the amino acid sequences represented by SEQ. ID. NO: 1 to SEQ. ID. NO: 4 of the present invention inhibit in vivo angiogenesis by inhibiting proliferation, migration and tube formation of vascular endothelial cells, and also inhibit proliferation and migration of cancer cells.

Accordingly, the present invention may provide a composition for inhibiting angiogenesis comprising the peptides of the present invention as effective ingredients, wherein the peptides may be included at a concentration of 1~500 uM with respect to total volume of the composition.

Further, a composition for inhibiting angiogenesis comprising one of peptides represented by SEQ. ID. NO: 1 to SEQ. ID. NO: 4 as an effective ingredient may be used as a pharmaceutical composition for inhibiting angiogenesis.

The composition for inhibiting angiogenesis of the present invention may include a peptide containing the amino acid sequence of the present invention singularly, or one or more pharmaceutically-acceptable carrier, excipient or diluent.

As used herein, the expression 'pharmaceutically-effective amount' is an amount of the bioactive ingredient which is sufficient to exhibit the intended biological or pharmacological activity when administered into animal or human. However, the pharmaceutically-effective amount may appropriately vary depending on the age, weight, health condition, gender, route of administration, or treatment period of a subject of administration.

As used herein, the expression 'pharmaceutically-acceptable' refers to a biologically-acceptable substance which does not generally cause gastroenteric trouble, allergic reaction such as dizziness, or any similar reaction, when administered to human. Examples of the carriers, excipients and diluents may include lactose, dextrose, sucrose, sorbitol, mannitol, xylitol, erithritol, maltitol, starchy, acacia rubber, alginate, gelatin, calcium phosphate, calcium silicate, cellulose, methyl cellulose, polyvinylpyrrolidone, water, methyl hydroxybenzoate, prophyl hydroxybenzoate, talc, magnesium stearate and preservative. Further, filler, anticoagulant, lubricant, wetting agent, fragrance, and preservative may be additionally included.

Further, the composition of the present invention may be prepared into a dosage form using known methods to provide rapid, continuous or delayed release of the active component since administration into a mammalian animal, in various forms for oral or parenteral administration.

The representative example of a parenteral dosage form includes an injection dosage form which may be in liquid or suspension state. The injection dosage form may be prepared using the known techniques using appropriate dispersion or wetting agent and suspension. For example, it is possible to prepare an injection dosage form by dissolving the respective ingredients in saline solution or buffer solution. The oral dosage form includes, for example, ingestible tablet, buccal tablet, troche, elixir, suspension, syrup and wafer, which may include in addition to the effective ingredient, diluent (e.g., lactose, dextrose, sucrose, mannitol, sorbitol, cellulose and/or glycin) and lubricant (e.g., silica, talc, stearic acid and magnesium or calcium salts thereof and/or polyethylene glycol). The dosage form may include a binding agent such as magnesium aluminum silicate, starch paste, gelatin, tragacanth, methylcellulose, natrium carboxymethylcellulose and/or poly vinylpyrrolidine, and depending on cases, may additionally include disintegrating agent such as starch, agar, alginate or sodium, absorbent, colorant, flavour and/or sweetening agent. The dosage form may be prepared by the conventional mixing, granulation or coating.

Further, the composition of the present invention may additionally include adjuvant such as preservative, water-dispersible powder, emulsification promoter, salts to adjust osmotic pressure or supplementing substance such as buffer, and other substances useful for treatment, and may be prepared into dosage form according to conventional methods.

The composition of the present invention may be administered by the routes including oral, percutaneous, subcutaneous, intravenous or intramuscular administration. An amount of the active ingredient administered may be appropriately selected by considering various factors including administration route, age, gender, weight and severity of a patient. Further, the composition of the present invention may be administered in parallel with a known compound to further increase the intended effect.

The administration route of the pharmaceutical composition of the present invention into human and animal may include oral administration, or parenteral administration such as intravenous, subcutaneous, intranasal, or intraperitoneal administration. The oral administration includes sublingual application. The parenteral administration may include injection method such as subcutaneous, intramuscular and intravenous injections and drop method.

According to the composition of the present invention, the total effective amount of peptide may be administered at a single dose, or by the fractionated treatment protocol in which the inhibitor is administered at multiple doses for a long period of time. The content of the effective ingredient may vary depending on diseases, but generally, the effective amount of 100 µg to 3,000 mg for one dose may be administered repeatedly several times a day for an adult. However, the concentration of treatment or administration may be determined based on not only the route of administration and frequency of treatment, but also various other factors including patient's age, weight, health condition, gender, severity of disease, diet and excretion rate. Given the above, those skilled in the art will be able to determine an appropriate effective amount of administration that suits a specific use such as anti-angiogenic activity, or treatment or prevention of angiogenesis-related diseases, and the composition of the present invention is not specifically limited to the specific dosage form, route of administration and method of administration that exhibit the effect of the present invention.

According to the present invention, a medicine for anti-angiogenic activity for prevention or treatment of angiogenesis-related diseases, comprising a pharmaceutical composition for anti-angiogenic activity according to the present invention as an effective ingredient may be provided, and a method for anti-angiogenic activity, comprising a step of administering a peptide containing the amino acid sequence according to the present invention into a mammalian animal except human with abnormally-continuing angiogenesis, may also be provided.

According to the present invention, the angiogenesis-derived diseases or diseases with abnormal angiogenesis may include, but not limited to: blood vessel formation-dependent cancers, benign tumors, rheumatoid arthritis, diabetic retinopathy, psoriasis, ocular angiogenesis disease, Osler-Webber Syndrome, myocardial angiogenesis, plaque neovascularization, telangiectasia, hemophilia arthropathy, angiofibroma, trauma granulation, intestinal adhesion, atherosclerosis, scleroderma, hypertrophic scar, cat scratch disease, *Helicobacter pylori* ulcers, dialysis transplantation vascular access stenosis and obesity.

Herein below, the examples of the present invention will be explained in greater detail. The following examples are provided to elucidate the present invention, but should not be construed as limiting.

Reference Example 1

Preparation of peptides, condition for cell culture, and statistics processing according to the present invention will be explained below.

<1-1> Preparation of Peptide According to the Present Invention

For the present invention, peptides were purchased from Thermo Fisher Scientific (Ulm, Germany) and Peptron Inc. (Daejeon, Korean). The purchased peptides were dissolved in DMSO and kept at −20 until use. Peptides were designed based on kringle 2 domain of the tissue type plasminogen activator and urokinase kringle domain with anti-angiogenic activity, considering antiparallel beta sheet structure, alpha helix structure and basic or acidic amino acid sequence, and named as: 1) FGNGSAY (FGN): TP1, 2) PWNSMILIGKVYTAQ (PWN): TP3, 3) PWCHVLKNRRLTWEY (PWCH): TP7, 4) PWNSATVLQQTYHAH (PWNSA): UP3, 5) PWCYVQVGLKPLVQE (PWCY): UP7. Considering the hydrophobicity of the above peptides, each experiment was conducted in parallel using FGNGSAY (TP1), which is lipid-soluble TK1-2 sequence with loop structure, as a control.

<1-2> Cell Culture

The HUVEC (human umbilical endothelial cell) was separated from the human cord by the known method of H. K. Kim et al., and cultured on serum-free EBM-2 or M199 medium for 4~6 hr immediately before the experiment.

<1-3> Statistical Processing

Statistical comparisons are based on student's t-test. A p value of less than 0.05 was considered significant. *, P<0.05; **, P<0.01. For the analysis of data obtained from in vivo Matrigel plug assay, we compared the differences between control group and other groups by Kruskal-Wallis test with Dunn's nonparametric multiple comparison to control the overall significance level at 0.05.

Example 1

Inhibitory Effect of the Peptides of the Invention on Endothelial Cell Proliferation Cell proliferation was measured by MTS assay. HUVECs were seeded to gelatin-coated 96-well plate at 1,000 cells/well and incubated in M199 supplement media for 48 h. After 48 h, cells were incubated in serum free M199 medium for 4 h, and then treated with each peptide at indicated concentrations for 30 min. Then, the cells were stimulated with 5% FBS and 10 ng/ml bFGF, and were incubated for 48 or 72 hr. Then, assessment of cell proliferation was done by MTS assay.

From this experiment, it was found that peptides TP3, TP7, UP3, and UP7 except TP1 inhibited growth of endothelial cells (see FIG. 1). TP3 inhibited growth of endothelial cells by reducing cell viability by approximately 26.7% at concentration of 100 μM, compared to the control group which was not treated with any peptide. UP3 had reduced cell viability by approximately 24% at concentration of 100 μM. TP7 and UP7 peptides showed strong inhibition effect in endothelial cell proliferation. TP7 decreased cell viability by 65.1% at concentration of 100 μM compared to the untreated control group, and UP7 showed cell viability reduced by 69.6%.

Example 2

Inhibitory Effect of the Peptides of the Invention on Endothelial Cell Migration In order to evaluate the effect of the peptides of the present invention on the cell migration, the present inventors conducted cell migration assay using modified Boyden chamber. HUVECs were treated with each peptide for 30 min and then, the cells were allowed to migrate toward VEGF (2~5 ng/ml). After 5 h, the migrated cells were fixed and stained with hematoxilin and eosin. The stained cells were photographed and counted.

Figure 2:
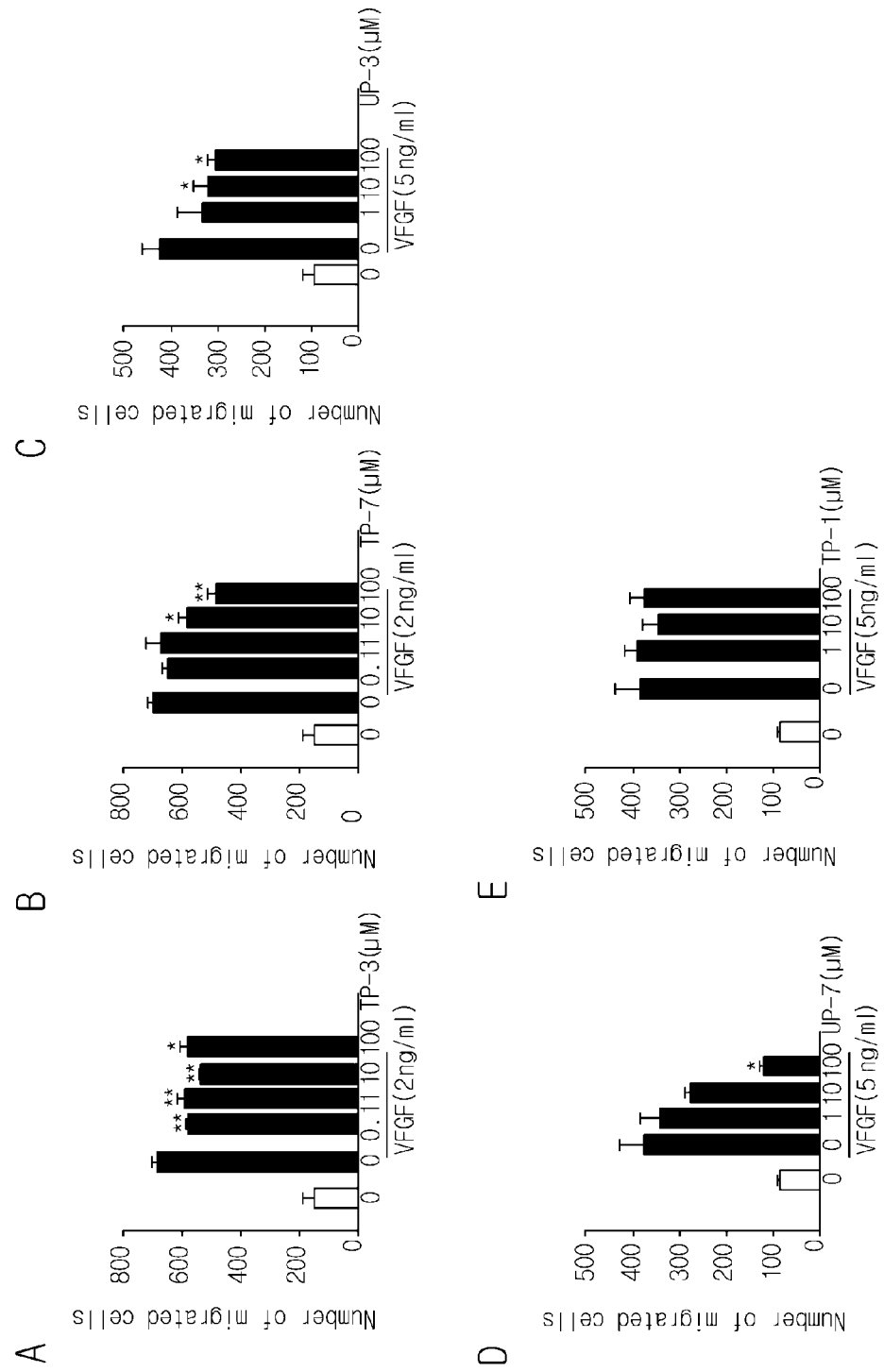
FIG. 2 is graphs illustrating the number of cells migrated, obtained after treating HUVECs with respective peptides at respective concentrations (0.1~100 μM) and inducing cell migration with VEGF (2~5 ng/ml) (A; TP3, B; TP7, C; UP3, D; UP7, E; TP1)

As shown in FIG. 2, TP7, UP3, UP7 peptides concentration-dependently inhibited VEGF-induced migration of endothelial cells, whereas TP1 did not inhibit the migration of endothelial cells at concentration of 100 μM. TP3 showed cell migration reduced by 15.4% compared to the number of migrated cells in the untreated control group at concentration of 0.1 μM, and also showed similar levels of inhibition effect at higher concentrations. TP7 concentration-dependently inhibited cell migration, and showed migration reduced by 31.4% compared to the untreated control group at concentration of 100 μM. UP3 showed significantly inhibition at concentration of 10 μM or above, and decreased migration by 28.6% at concentration of 100 μM. UP7 drastically decreased cell migration by approximately 72% at concentration of 100 μM, showing potent inhibitory effect on endothelial cell migration.

Example 3

Inhibitory Effect of the Peptide of the Present Invention on Tube Formation

In order to investigate the effect of the peptides of the present invention on the tube formation, tube formation assay was performed as described previously.

Chilled Matrigel (150 µl, BD Bioscience) was placed in a pre-chilled 48-well plate and incubated for 30 min at 37° C. HUVECs were treated with each peptide for 30 min and then added to the top of the solidified Matrigel. After 19 h of incubation, the tubes formed were photographed. Images were analyzed using Image J <http://rsb.info.nih.gov/ij/> to determine tube lengths.

That is, the incubated HUVEC with a new serum-free medium was incubated for 2~4 hr and harvested the cells. After treating the harvested cells at 100 µM with the respective peptides for 30 min, the cells on the hardened Matrigel was incubated for 11~19 hr, while observing the degree of tube formation, and measured and calculated the lengths of the tubes formed. As a result, it was observed that all the tested peptides, while varying degrees, inhibited tube formation. TP3 inhibited tube formation by approximately 70% compared to the control group, and TP7 showed strong inhibition by decreasing tube formation by approximately 93%. UP3 decreased tube formation by 47%, and TP1 by approximately 37%. Interestingly, UP7 peptides, which have potent inhibitory effect on migration and proliferation of the endothelial cells, did not show any inhibitory effect on the tube formation of endothelial cells (see FIG. 3).

Example 4

Inhibition of In Vivo Angiogenesis by the Peptides of the Present Invention in Matrigel Plug Assay In order to examine the anti-angiogenic activity of the respective peptides in vivo, Matrigel plug assay was performed. 7-week-old C57/BL6 mice (SLC, Japan) were injected subcutaneously in the midventral abdominal region with 0.6 ml of Matrigel containing the bFGF (100 ng/ml), VEGF (100 ng/ml) and heparin (15 unit) with or without peptide. After 7 days, mice were sacrificed by inhalation of $CO_2$ gas and the Matrigel plugs were removed and photographed. To evaluate the formation of vessels, the amount of hemoglobin was quantified using Drabkin's reagent (Sigma). The Matrigel plug was sonicated in RBC lysis buffer (Sigma) and centrifuged at 14000 rpm for 20 min. The supernatant was mixed with Drabkin's reagent and incubated for 3 min. Then, absorbance was measured at 540 nm.

As illustrated in FIG. 4, not all the transplanted Matrigel plugs showed uniform angiogenesis, with some plugs showing excessive amount of hemoglobin exceeding 500 mg/dl. The untreated control group and TP1, TP3, UP3-treated groups showed such plugs with excessive hemoglobin, while the groups treated with TP7 and UP7, which have relatively high anti-angiogenic activity, did not exhibit such plugs. TP7-treated group showed a median value of hemoglobin amount approximately reduced to 51% without statistical significance, when the hemoglobin amount of TP-7 (median: 37.3 mg/dl, entire range; 11.8~82.8 mg/dl) was compared to the untreated control group (median; 72.3 mg/dl, entire range; 6.8~941.8 mg/dl). UP3-treated group also showed reduced median value (median; 4.8 mg/dl, entire range 1.8~586.8 mg/dl) of hemoglobin amount compared to the control group ($P<0.1$, insufficient statistical significance). UP7-treated group showed remarkably reduced hemoglobin amount (hemoglobin) (median; 16.3 mg/dl, entire range 5.8~31.8 mg/dl) with statistical significance ($P<0.05$), thereby indicating that UP-7 has the most potent inhibitory activity against in vivo angiogenesis. Taken together, these results suggest that the peptides of the present invention can be used as candidates for potent angiogenesis inhibitors.

Example 5

Inhibitory Effect of the Peptides of the Present Invention on Cancer Cell Proliferation The Effect of the peptides on cancer cell proliferation was investigated using A549 lung cancer cell line. A549 cells were seeded to 96 well plate at 1,000 cells/well and incubated in DMEM medium containing 10% FBS for 48 h. After treatment of each peptide for 30 min, the proliferation of cancer cells was stimulated by 5% FBS alone. After each incubation time, MTS solution was added to each well and incubated for 2 h. Assessment of proliferation was determined by measurement of absorbance at 490 nm.

Figure 5:
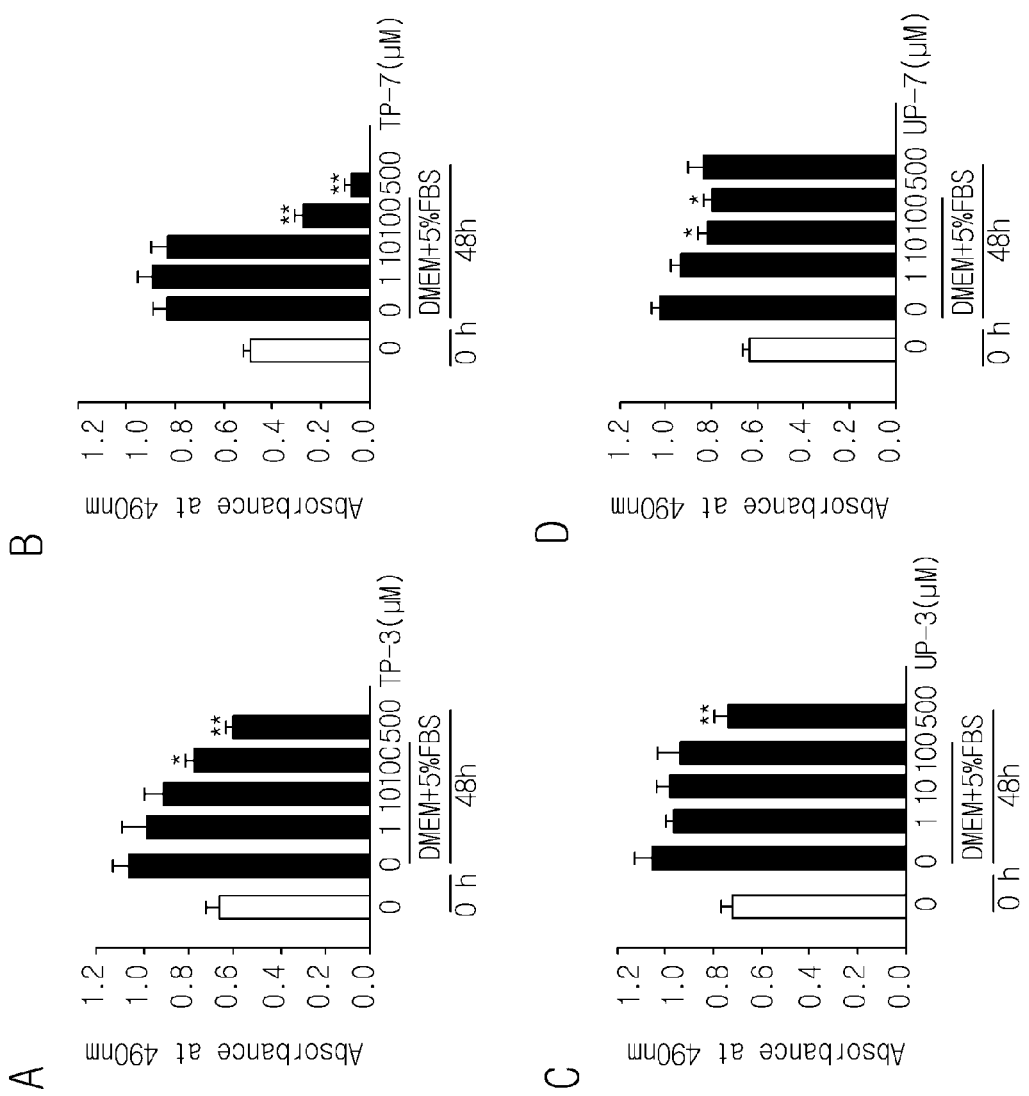
FIG. 5 is graphs illustrating MTS assay on the growth of cells, after seeding human lung cancer cell lines (i.e, A549) into 96-well plate, incubating for 48 hr, pre-treating the cells with respective peptides for 30 min per concentration, and then incubating the cells with 5% FBS for another 48 hr. (A; TP3, B; TP7, C; UP3, D; UP7)

After incubation with the peptides for 48 hr, all the peptides, i.e., TP3, TP7, UP3, UP7 concentration-dependently inhibited proliferation of A549 cancer cells (FIG. 5). UP3, although not showing significant inhibition at concentration of 100 µM, did show inhibitory effect on cancer cell growth by decreasing the cell survival rate by approximately 30.3% at the concentration of 500 µM compared to the untreated control group cells. UP7 inhibited cancer cell growth approximately by 21.8% at concentration of 100 µM. TP3 showed relatively marked inhibitory effect on cancer cell growth by showing cell survival rate reduced by approximately 26% at concentration of 100 µM, and by 43% at 500 In particular, TP7 showed a potent inhibitory effect on cancer cell growth by 67% growth inhibition at 100 µM and 91% at 500 µM. Thus, it was confirmed that the peptides of the present invention have also marked inhibitory effect on the growth of cancer cells.

Example 6

Figure 6:
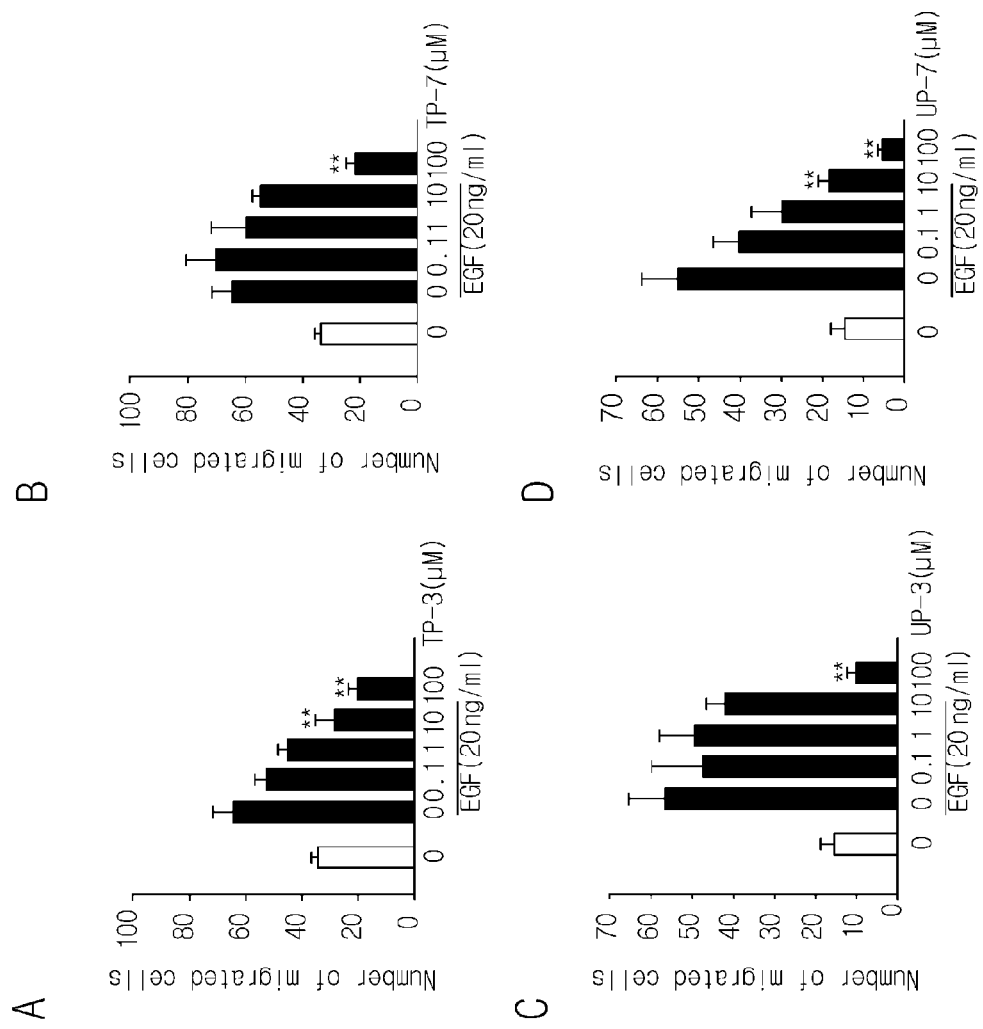
FIG. 6 is graphs illustrating the number of cells migrated, observed after treating human breast cancer cell lines (i.e., MDAMB 231) with respective peptides for 30 min, and inducing migration of cells using EGF (20 ng/ml) (A; TP3, B; TP7, C; UP3, D; UP7).

Inhibitory Effect of the Peptides of the Present Invention on Cancer Cell Migration In order to investigate the effect of the respective peptides on cancer cell migration, modified Boyden chamber assay was conducted. MDAMB231 breast cancer cells have EGF receptor and have ability to migrate and metastasize. When MDAMD231 cells were induced by EGF in the presence of the peptide, TP3, TP7, UP3 and UP7 peptides concentration-dependently inhibited the migration of the breast cancer cell (FIG. 6). TP3 decreased cell migration approximately by 30% at concentration of 1 µM, and approximately by 69.4% at concentration of 100 µM compared to the untreated control group. Treatment with TP7 resulted in reduced cell migration by 66.3% at concentration of 100 µM. UP3 and UP7 also showed cell migration reduced by 81% and 88%, respectively, at concentration of 100 µM, in which UP7 particularly showed approximately 66% reduction even at concentration of 10 µM, thereby showing the most potent inhibitory effect. The above results also support that the peptides of the present invention can inhibit cancer cell metastasis.

While several particular formulations have been described above, it will be apparent that various modifications and combinations of the formulations detailed in the text can be made without departing from the spirit and scope of the invention. Accordingly, the description of the exemplary embodiments of the present invention is intended to be illustrative, and not to limit the scope of the claims, and many alternatives, modifications, and variations will be apparent to those skilled in the art.

The invention claimed is:

1. A composition for decreasing angiogenesis, the composition comprising the isolated peptide selected from the group consisting of SEQ ID NO:3 and SEQ ID NO:4 as an effective ingredient, and a pharmaceutically acceptable carrier, excipient or diluent, wherein the peptide decreases angiogenesis.

2. The composition set forth in claim 1, comprising 1 to 500 μM of peptide concentration with respect to the total volume of the composition.

3. A method for decreasing angiogenesis in a mammal with abnormally-continuing angiogenesis, the method comprising administering the composition set forth in claim 1 into the mammal.

4. The method according to claim 3, wherein the mammal is human.

5. The method according to claim 3, wherein the composition is administered orally or parenterally.

6. The method according to claim 3, wherein the mammal suffers from a disease selected from the group consisting of benign tumors, rheumatoid arthritis, diabetic retinopathy, psoriasis, Osler-Webber Syndrome, plaque neovascularization, telangiectasia, hemophilia arthropathy, angiofibroma, trauma granulation, intestinal adhesion, atherosclerosis, scleroderma, hypertrophic scar, *Helicobacter pylori* ulcers, dialysis transplantation vascular access stenosis and obesity.

7. A method for decreasing migration or tube formation of endothelial cells comprising contacting the cells with the composition according to claim 1.

8. The method according to claim 7, wherein the decreasing occurs in vivo.

9. A method for decreasing proliferation or migration of cancer cells in vitro comprising contacting the cells with the composition according to claim 1.

10. A method treating a mammal suffering from a disease selected from the group consisting of benign tumors, rheumatoid arthritis, diabetic retinopathy, psoriasis, Osler-Webber Syndrome, plaque neovascularization, telangiectasia, hemophilia arthropathy, angiofibroma, trauma granulation, intestinal adhesion, atherosclerosis, scleroderma, hypertrophic scar, *Helicobacter pylori* ulcers, dialysis transplantation vascular access stenosis and obesity, comprising administering the composition according to claim 1 to the mammal suffering therefrom.

11. The method according 10, wherein the mammal is human.

12. The method according to claim 10, wherein the composition is administered orally or parenterally.

* * * * *

SEQUENCE LISTING

<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Artificially synthesized

<400> SEQUENCE: 1

Pro Trp Asn Ser Met Ile Leu Ile Gly Lys Val Tyr Thr Ala Gln
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Artificially synthesized

<400> SEQUENCE: 2

Pro Trp Cys His Val Leu Lys Asn Arg Arg Leu Thr Trp Glu Tyr
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Artificiallly synthesized

<400> SEQUENCE: 3

Pro Trp Asn Ser Ala Thr Val Leu Gln Gln Thr Tyr His Ala His
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Artificially synthesized

<400> SEQUENCE: 4

Pro Trp Cys Tyr Val Gln Val Gly Leu Lys Pro Leu Val Gln Glu
1               5                   10                  15